US006280545B1

(12) United States Patent
Kanesaka

(10) Patent No.: US 6,280,545 B1
(45) Date of Patent: Aug. 28, 2001

(54) METHOD OF FORMING BALLOON CATHETER

(76) Inventor: Nozomu Kanesaka, 81 Greenwoods Rd., Old Tappan, NJ (US) 07675

( * ) Notice: Subject to any disclaimer, the term of this patent is extended or adjusted under 35 U.S.C. 154(b) by 0 days.

(21) Appl. No.: 09/496,664

(22) Filed: Feb. 3, 2000

(51) Int. Cl.[7] ............................ B32B 31/26; A61M 25/10
(52) U.S. Cl. .................................. 156/84; 156/85; 156/86; 156/381; 604/264; 604/523; 604/509; 604/96.01; 604/101.05; 606/194
(58) Field of Search .................................. 156/84–86, 198, 156/282, 290, 381; 604/264, 523–527, 508–509, 96.01, 101.01, 101.05, 103.03, 103.01, 103.02, 103.11, 104, 532–534, 538; 606/191–192, 194; 264/342 R, DIG. 6

(56) References Cited

U.S. PATENT DOCUMENTS 5,549,552 * 8/1996 Peters et al. ........................... 604/96

5,569,195 * 10/1996 Saab ....................................... 604/96

* cited by examiner

*Primary Examiner*—Michael W. Ball
*Assistant Examiner*—Jessica Rossi
(74) *Attorney, Agent, or Firm*—Kanesaka & Takeuchi

(57) ABSTRACT

A balloon catheter is formed by a heat shrinkable tube. In the method, a rod member is inserted into the shrinkable tube, and parts of the shrinkable tube are heated so that the parts of the shrinkable tube shrink to thereby form end portions of at least one balloon portion while a portion away from the end portions does not shrink. Two end portions of the balloon portion are processed to have a small diameter. Then, the rod member is removed from the shrinkable tube, and a catheter shaft is inserted into the balloon portion to completely pass therethrough. Finally, the two end portions of the balloon portion are fixed onto the catheter shaft. Since the heat shrinkable tube with the constant thickness is used, high quality catheter can be formed without fail.

12 Claims, 6 Drawing Sheets

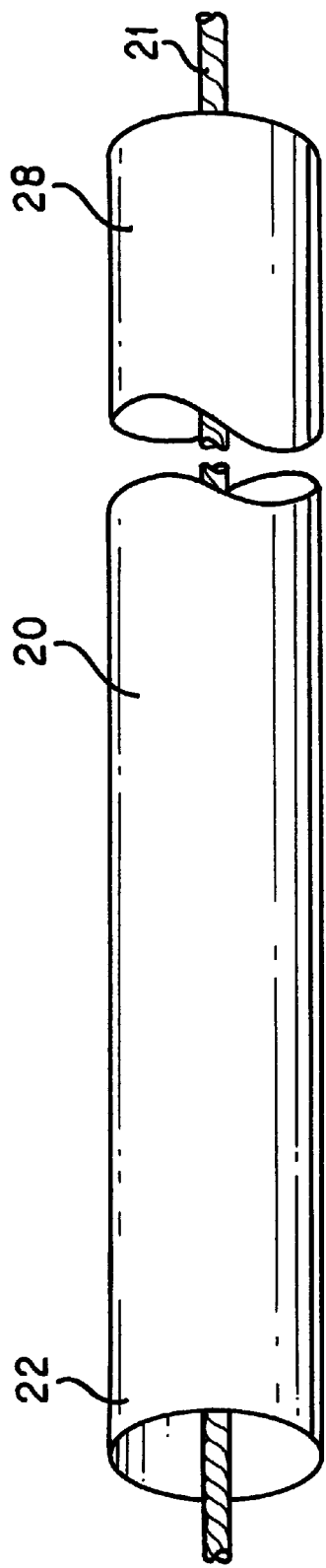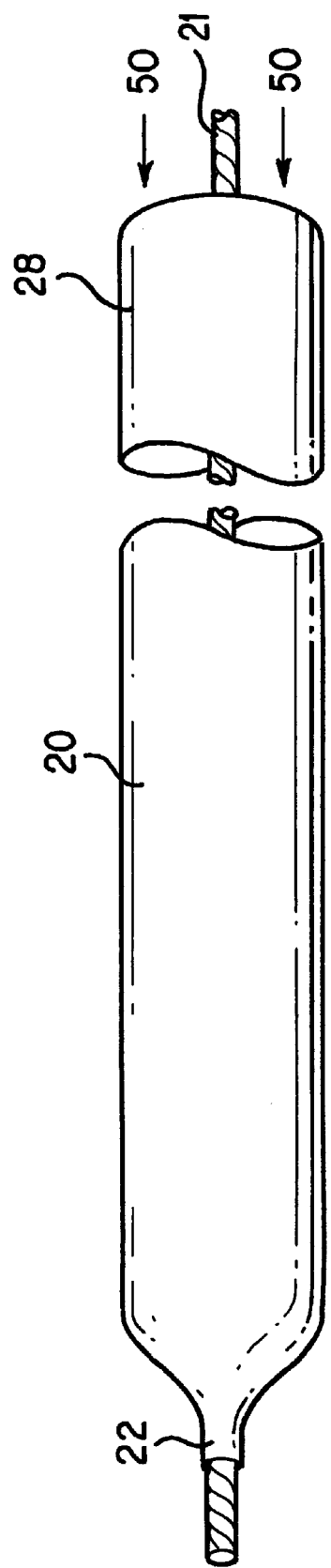

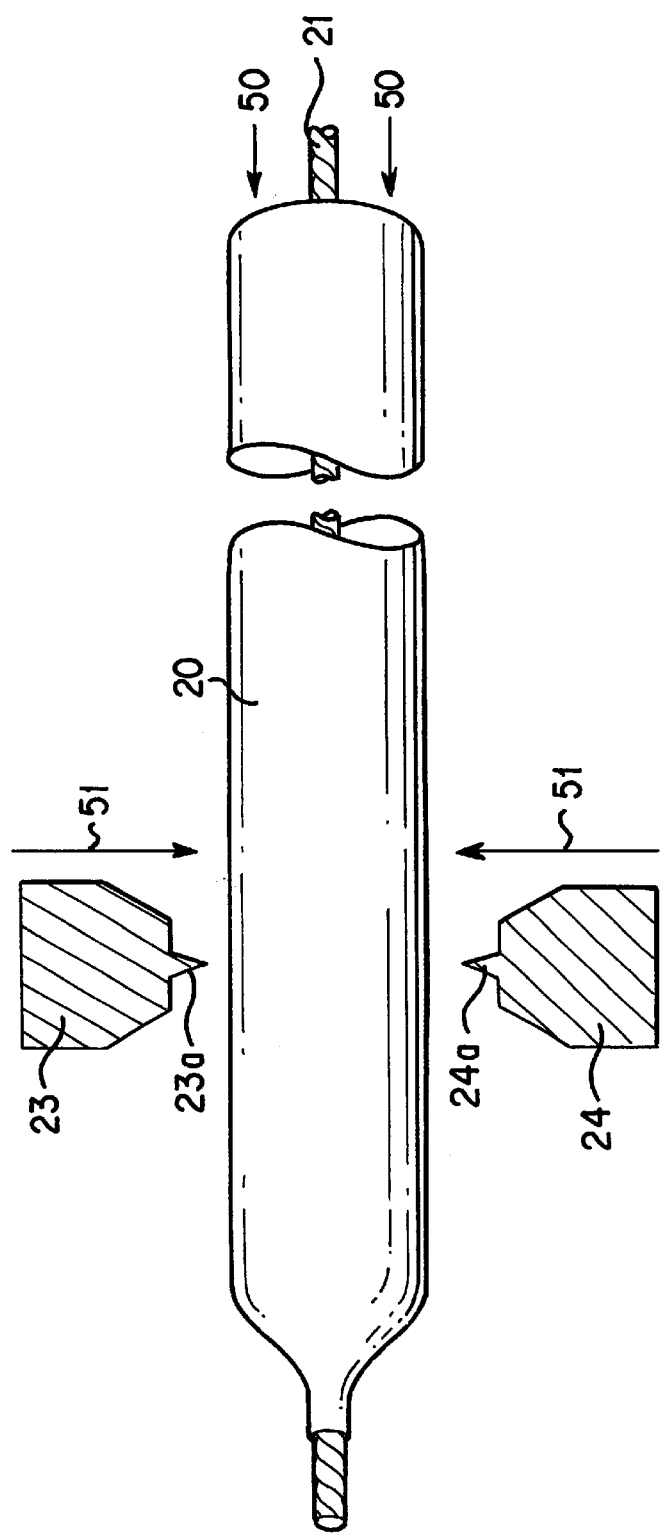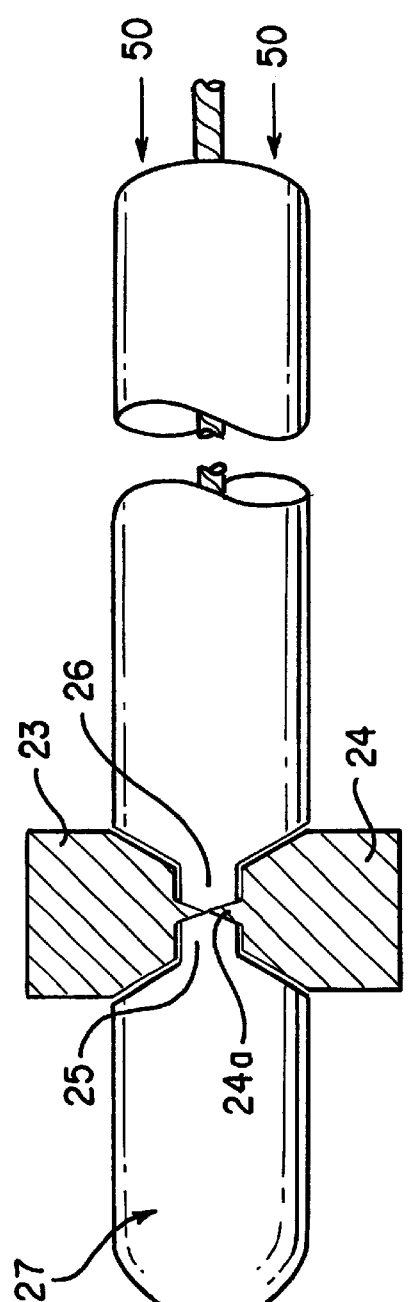
FIG. 9
FIG. 10

METHOD OF FORMING BALLOON CATHETER

BACKGROUND OF THE INVENTION AND RELATED ART STATEMENT

The present invention relates to a method of forming a balloon catheter to be used in a percutaneous transluminal coronary angioplasty (PTCA) procedure and/or in a stent implantation into a patient's body lumen.

A balloon catheter has been widely used for vascularization of a coronary artery. In this case, a balloon attached to a catheter is delivered into a coronary artery to enlarge a stenosis, i.e. constriction in the coronary artery. Since a large pressure is applied to the balloon to enlarge the stenosis, the balloon is required to withstand high inner pressure.

Conventionally, a balloon used for a balloon catheter has been made by blow molding method. When the blow molding method is used, as shown in FIG. 13, a balloon member 102 having a diameter substantially the same as that of an inner tube member 101 is disposed over the inner tube member 101. Then, as shown in FIG. 14, the inner tube member 101 with the balloon member 102 thereon is placed in a mold 104, which includes an inner chamber 105 in a shape of an inflated balloon and heating elements 106.

Thereafter, the mold 104 is heated by the heating elements 106 in the mold 104, and a gas for blowing the balloon member 102 is supplied from the inner tube 101. The balloon member 102 is inflated by the gas supplied from the inner tube 101 and entered inside the balloon member 102 through a communication hole 103 in the inner tube member 101. The balloon member 102 is inflated to abut against the wall portion of the mold 104 as shown in FIG. 15. Then, end portions 107, 108 of the balloon member 102 are adhered to the inner tube member 101 by an adhesive or the like. The end portions 107, 108 of the balloon member 102 may be fixed to the inner tube member 101 before blow molding the balloon member.

In the conventional blow molding method, however, there is a problem. Namely, since the balloon member, which has a shape of a tube member with the small diameter before blow molding, is blown by the gas supplied thereinto to have a shape of the inflated balloon, degree of inflation of the balloon member is different according to the portions of the balloon member, resulting in uneven thickness. Namely, although the thickness of the balloon member before blow molding is substantially constant, the thickness of the inflated balloon member may be partly different. As a result, if high pressure is applied to the balloon member in use, the balloon member may be torn or broken.

Also, in the conventional balloon catheter, the quality of the balloon catheter can be checked only after the balloon member is formed.

The present invention has been made in view of the above problems, and an object of the present invention is to provide a method of forming a balloon catheter, wherein the high quality balloon catheter can be formed easily at a low cost.

Another object of the invention is to provide a method of forming a balloon catheter as stated above, wherein a balloon portion with a constant thickness can be formed without fail.

Further objects and advantages of the invention will be apparent from the following description of the invention.

SUMMARY OF THE INVENTION

In the method of forming a balloon catheter of the invention, a heat shrinkable tube is used. The heat shrinkable tube used in the invention has a predetermined diameter in a normal condition i,e. normal pressure and temperature, and a thickness substantially constant throughout the entire length thereof. When heat is applied to the heat shrinkable tube, a portion where the heat is applied shrinks. The heat shrinkable tube is made of a material same as or similar to a regular material for making a balloon portion of the balloon catheter. Since the process for making the heat shrinkable tube is known in the art, the explanation thereof is omitted herein.

In the invention, the heat shrinkable tube has a first diameter in the normal condition, which is substantially the same as the diameter of a balloon portion of the balloon catheter when it is expanded.

In the method of the invention, a rod member, preferably a metal rod member so that the shrinkable tube when heated does not stick to the rod member, is inserted into the shrinkable tube. Then, at least one part of the shrinkable tube is heated so that the part of the shrinkable tube shrinks to have a second diameter to thereby form an end portion of one balloon portion while a portion away from the end portion has the first diameter as it is. Namely, when the shrinkable tube is heated, a part of the shrinkable tube close to the non-heating portion does not shrink too much, but an end portion of the tube shrinks largely and is disposed onto the rod.

In the invention, two end portions of the shrinkable tube are processed at the same time or different time to have the second diameter by heat shrinking.

Then, the rod member is removed from the balloon portion, and a catheter shaft is inserted into the balloon portion to completely pass therethrough. Thereafter, the two end portions of the balloon portion are fixed onto the catheter shaft, so that the balloon catheter is formed.

In the method of the invention, since the heat shrinkable tube formed already is used, the quality of the balloon portion is assured. Namely, the quality of the shrinkable tube is generally good, i.e. the thickness and strength are substantially constant throughout the entire length thereof. Nevertheless, in case the quality of the shrinkable tube is questionable, the quality thereof can be checked before forming the balloon portion. Thus, in the method of the invention, the high quality heat shrinkable tube can only be used in forming the balloon catheter.

In this respect, in the conventional method, i.e. blow molding method, the balloon portion is expanded in a mold each time. Thus, although the good quality member is used, the quality of the balloon portion formed by blow molding is slightly different in each blow molding. The quality of the balloon can be checked after completion of the balloon. If the quality of the balloon portion is not good, the balloon catheter must be discarded. In the method of the invention, however, since blow molding is not used and the end portions are simply processed to shrink by heating, the balloon portion with high quality can be formed constantly. Thus, the productivity used in the method of the invention is high.

In one embodiment of the invention, two end portions of the balloon portion are formed by heat-shrinking the shrinkable tube. In this case, an outer periphery of a middle portion between the two end portions is insulated from the two end portions, and then, heat is applied so that the two end portions are heated to shrink while the middle portion is insulated from being heated. In this case, a gas may be supplied inside the shrinkable tube before heating to keep a shape of the shrinkable tube.

In another embodiment, after the rod member is inserted into the shrinkable tube, the diameter of one end of the shrinkable tube is reduced or the one end is heat-shrunk. The one end of the shrinkable tube may be fixed onto the rod member by string, tape or other means. Then, a gas is provided inside the shrinkable tube to keep the shape of the shrinkable tube in an inflated condition. Thereafter, a part of the shrinkable tube is heated so that one end portion of one balloon portion and one end portion of another balloon portion are formed at the same time. Namely, a plurality of parts of the shrinkable tube is heated at substantially the same time to form a plurality of balloon portions at substantially the same time.

In this case, heat is allied by heat pads formed of a plurality of heat segments. Namely, the heat segments are disposed onto the rod member through the shrinkable tube while shrinking the shrinkable tube. Preferably, the heat segments are pressed against the rod member to thereby cut the balloon portions away from each other at the same time.

BRIEF DESCRIPTION OF THE DRAWINGS

FIG. 7 is a schematic side view showing an elongated heat shrinkable tube according to a second embodiment of a method of the invention;

FIG. 8 is a schematic side view showing that one end of the heat shrinkable tube shown in FIG. 7 is adhered to a metal rod member;

FIG. 9 is a schematic side view showing that a pair of movable heating members is approaching the heat shrinkable tube shown in FIG. 8;

FIG. 10 is a schematic side view showing that a balloon member is formed from the heat shrinkable tube by the movable heating members;

DETAILED DESCRIPTION OF PREFERRED EMBODIMENTS

Hereinafter, embodiments of the present invention will be explained with reference to the accompanying drawings.

Figure 1:
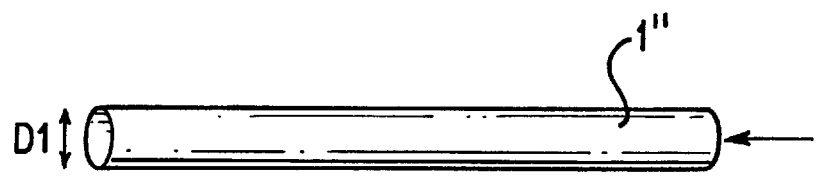
FIG. 1 is a schematic side view showing a tube member before forming a heat shrinkable tube used in the present invention.
Figure 2:
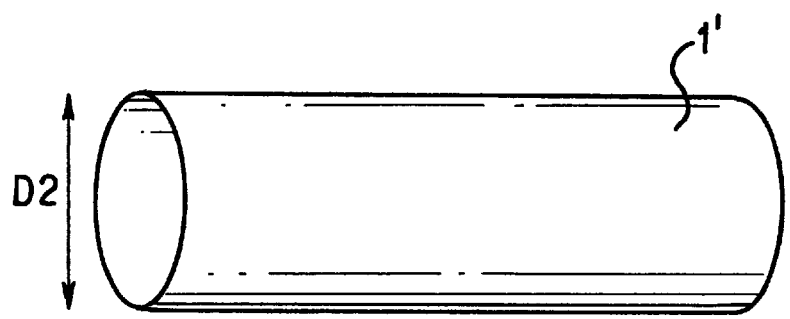
FIG. 2 is a schematic side view showing the heat shrinkable tube used in the invention.

According to the method of forming a balloon catheter of the present invention, a heat shrinkable tube 1' already known in the art and shown in FIG. 2 is used. The heat shrinkable tube 1' is formed from a tube 1" having a first diameter D1, as shown in FIG. 1. As a material for the heat shrinkable tube 1', polyethylene, PET (polyethylene terephthalate), polyurethane, and so on, which is used for forming a conventional balloon catheter, may be used.

The heat shrinkable tube 1' is formed by enlarging the diameter of the tube 1" by known method, such as drawing the tube 1" while heating, and so on. When the tube 1" is processed to form the heat shrinkable tube 1', the diameter and the thickness of the heat shrinkable tube 1' are constant throughout the entire length thereof. The heat shrinkable tube 1' keeps its shape as it is in the normal temperature and pressure.

Namely, the tube 1" with the diameter D1 is enlarged to form the heat shrinkable tube 1' with the second diameter D2, i.e. approximately four to six times of the first diameter D1. For example, the first diameter D1 of 0.022 inches (0.558 mm) may be enlarged to the second diameter D2 of 0.098 to 0.15 inches (2.5 to 4 mm). Also, the first diameter D1 of 0.065 inches (1.651 mm) may be enlarged to the second diameter D2 of 0.31 to 0.39 inches (8 to 10 mm).

The heat shrinkable tube 1' formed according to the conventional method may be used in the method of the invention without checking the quality thereof. However, if necessary, the quality of the heat shrinkable tube 1' may be checked before forming a balloon catheter.

Figure 3:
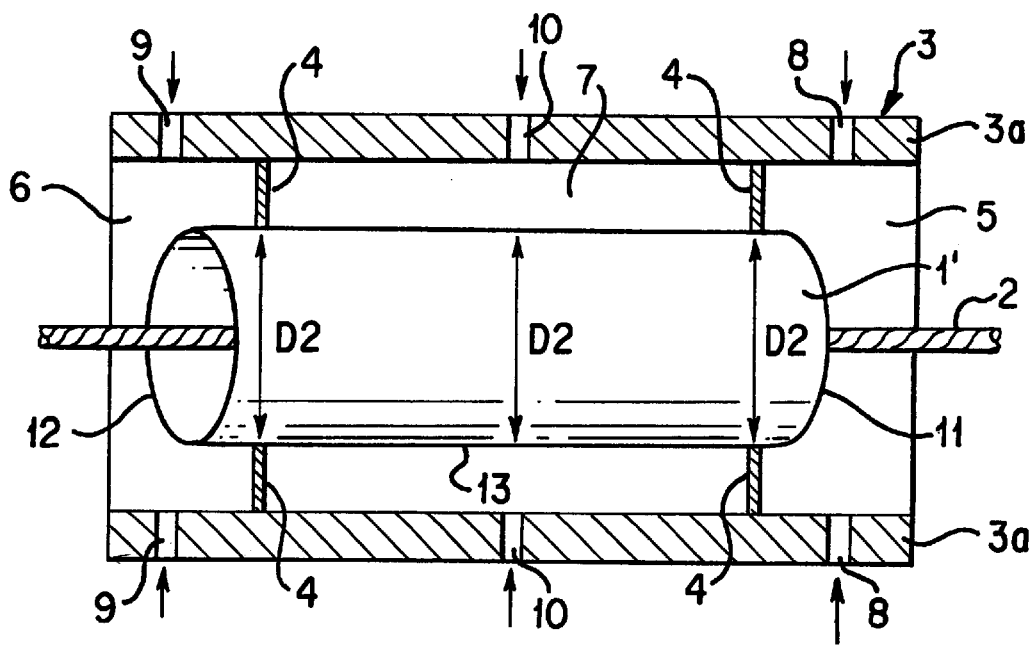
FIG. 3 is a schematic, partly sectional view showing that the heat shrinkable tube of FIG. 2 is placed in a mold according to the first embodiment of the method of the present invention.

When the balloon catheter is prepared, after preparing the heat shrinkable tube 1' with the second diameter D2, as shown in FIG. 3, a metal rod member 2 is inserted into the shrinkable tube 1', and the shrinkable tube 1' including the metal rod member 2 therein is placed inside a mold 3. The metal rod member 2 has a coating, such as Teflon, thereon so that in case the shrinkable tube 1' shrinks and is deposited onto the rod member 2 at the end portions to thereby form the balloon member 1, the end portions do not adhere the rod member 2.

The mold 3 according to the first method of the present invention has a cylindrical shape, and a pair of heat insulating members 4 is disposed in the vicinity of end portions of the mold 3. Each insulating member 4 has a circular opening in a center thereof for introducing the shrinkable tube 1' therein. The diameter of the opening of the insulating member 4 is approximately the same as the second diameter D2 of the shrinkable tube 1'.

The insulating members 4 generally divide an interior of the mold 3 into three areas, i.e. end areas 5 and 6 and middle area 7. The end area 5 or 6 is located between an end of the mold 3 and the nearest insulating member 4, and the middle area 7 is located between the insulating members 4. Also, inlets 8, 9 and 10 are formed in a wall portion 3a of the mold 3, such that the inlets 8 and 9 respectively communicate with the end areas 5 and 6, and the inlets 10 communicate with the middle area 7.

As shown in FIG. 3, when the shrinkable tube 1' with the metal rod member therein 2 is inserted into the mold 3, ends 11, 12 of the shrinkable tube 1' are respectively located in the end areas 5 and 6, and a middle portion 13 of the shrinkable tube 1' is located in the middle area 7.

Figure 4:
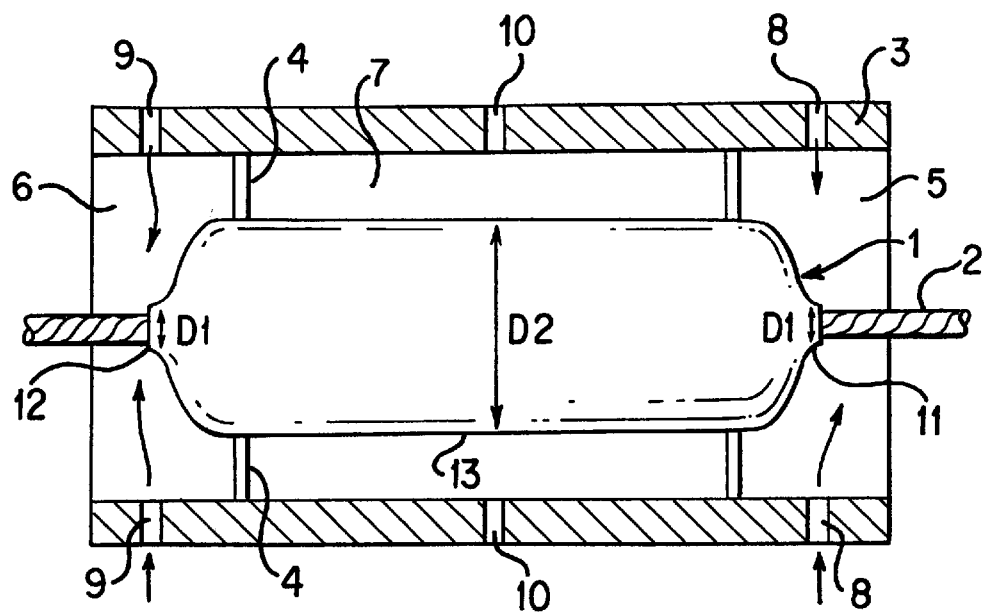
FIG. 4 is a schematic, partly sectional view showing that the heat shrinkable tube in FIG. 3 is partly heated in the mold to form a balloon member.

Then, heated air or gas is supplied from the inlets 8 and 9 to heat the end areas 5 and 6, and cool air or gas is supplied into the middle chamber 7 from the inlets 10, so that the ends 11, 12 of the shrinkable tube 1' are only heated to thermally shrink and contact the metal rod member 2, whereby a balloon member 1 is formed. In this state, as shown in FIG. 4, the diameter at each end 11 or 12 becomes the first diameter D1. When the end areas 5 and 6 are heated by the heated air supplied from the inlets 8 and 9, and the middle area 7 is cooled by the cool air supplied from the inlets 10, the insulating members 4 prevent the heated air and the cool air from mixing together. The middle portion 13 of the balloon member 1 does not shrink, and keeps the second diameter D2.

In the invention, in order to keep the metal rod member 2 in the middle of the shrinkable tube 1' in heating the shrinkable tube, the rod member 2 may be hollow and have radial holes. The radial holes are located inside the shrinkable tube 1' and air is supplied inside the shrinkable tube 1' to thereby keep the rod member 2 in the middle of the shrinkable tube 1'.

Figure 5:
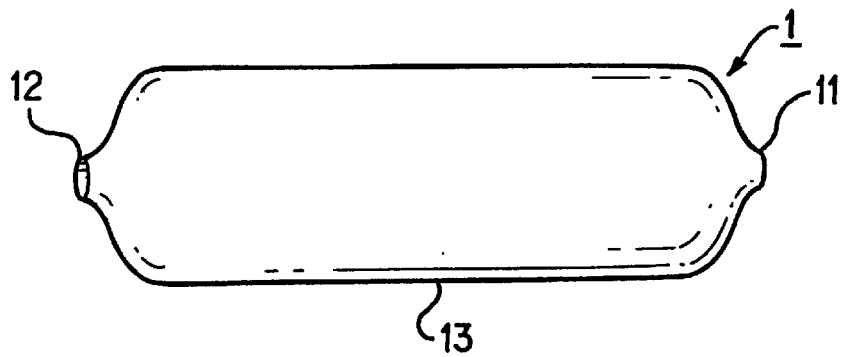
FIG. 5 is a schematic side view showing the balloon member without a metal rod member.
Figure 6:
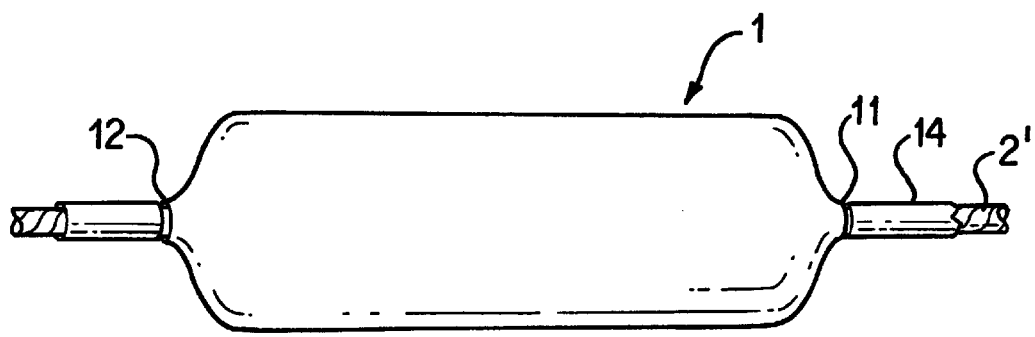
FIG. 6 is a schematic side view showing that the balloon member is placed over a catheter shaft to form a balloon catheter.

After shrinking the ends 11, 12 of the shrinkable tube 1', the shrinkable tube 1' becomes the balloon member 1 having a shape as shown in FIG. 4. Then, the balloon member 1 placed over the metal rod member 2 is removed from the mold 3, and the metal rod member 2 is removed from the balloon member 1, as shown in FIG. 5. Thereafter, a metal rod member 2' is inserted into a hollow catheter shaft 14 which has a diameter approximately the same as the first diameter D1, and the catheter shaft 14 containing the metal rod member 2' therein is inserted into the balloon member 1 as shown in FIG. 6, so as to form a balloon catheter.

The ends 11, 12 of the balloon member 1 are fixed to the catheter shaft 14 by heating the ends 11, 12 while utilizing the heat-shrink property thereof, or can be fixed to the catheter shaft 14 by an adhesive. Even if the ends 11, 12 are attached to the shaft 14 by heating the ends, the ends 11 and 12 are further applied with the adhesive to securely fix the balloon member 1 to the catheter shaft 14. Tapes may be further used to fix the ends 11, 12 of the balloon member 1 to the catheter shaft 14.

Although the cylindrical mold with a pair of ring-shaped insulating members is used in the aforementioned embodiment, the shapes, arrangement, and configuration of the mold and the insulating members may be modified as long as only the end portions of the heat shrinkable tube are heated and a middle portion thereof is not heated.

Further, although the heated air or gas is supplied from the inlets formed in the wall portion of the mold in the embodiment, heating means is not limited to this, and may be other heating means.

FIGS. 7 through 12 show a second embodiment of the method of the invention, wherein a plurality of balloons can be formed from a single, elongated heat shrinkable tube.

In the second embodiment, as shown in FIG. 7, an elongated heat shrinkable tube 20, which is known in the art and formed as described in the first embodiment, is prepared. A metal rod member 21 is inserted into the tube 20 to pass throughout the tube 20. One end 22 of the heat shrinkable tube 20 is attached to the metal rod member 21, for example, by heat shrinking the tube 20, as shown in FIG. 8. The tube 20 may be simply fixed to the rod member 21 by a string or tape.

Then, air is supplied into the hollow portion of the tube 20 as shown by arrows 50 in the figures. Air may be supplied into the tube 20 through the rod member 21. Namely, the rod member 21 is formed to be hollow and have radial holes. The radial holes are located inside the tube 20, and air is supplied to thereby keep the rod member 2 in the middle of the tube 20.

In the second embodiment, a pair of movable heat members or pads 23, 24 is provided respectively above and below the tube 20. The heat members 23, 24 have heat elements therein, so that the heat members 23, 24 can be heated immediately to a desired temperature. Each of the movable heat members 23, 24 has a semicircular concave at one end, when viewed from an end of the tube 20, i.e. from left or right side in FIG. 9. Thus, when the heat members 23, 24 are closed or joined together, a circular hole for forming end portions of the balloons is formed. The movable heat member 23 or 24 has a trapezoidal shape in section at an inner end with a projection 23a or 24a to form end portions of balloon portions. The upper and lower heat members 23, 24 are arranged symmetrically with respect to the tube 20. However, the shapes of the heat members or pads for forming the ends of the balloon portions are not limited to the shape in this embodiment, and can be modified as long as the end portions of the balloon portions are formed.

In use, the movable heat members 23, 24 are moved toward the tube 20 at a desired position on the tube 20 as shown by arrows 51 in FIG. 9. When the heat members 23, 24 abut against each other or pressed against the rod member 21 through the tube 20, the heat members 23, 24 are heated, so that the tube 20 shrinks along the shape of the heat members 23, 24 and portions of the tube 20 are cut by the projections 23a, 24a. Thus, the end portions 25, 26 of the balloon portions are formed.

On the other hand, the heat members 23, 24 may be heated to a predetermined temperature in advance, so that when the heat members 23, 24 contact the tube 20 while moving toward the rod member 21, the tube 20 shrinks slowly. The tube 20 can be cut when the projections 23a, 24a abut against the rod member 21.

Figure 11:
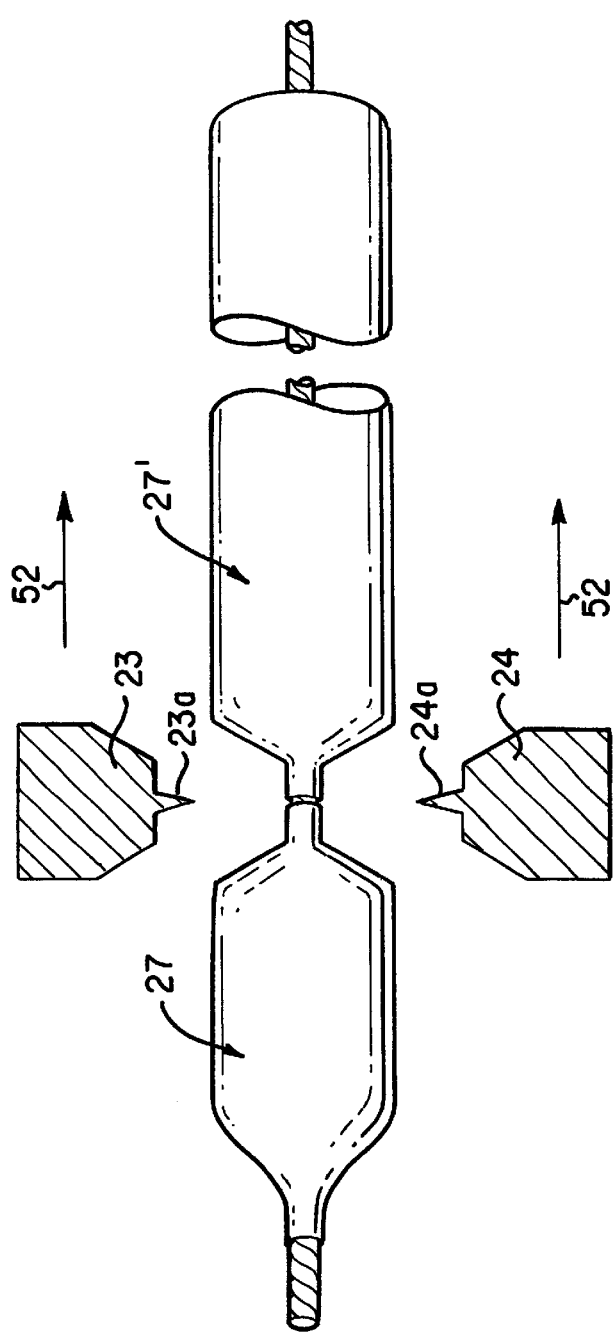
FIG. 11 is a schematic side view showing that the movable heating members are moved so as to form another balloon member from the heat shrinkable tube.

In the embodiment, since the end 22 of the tube was fixed onto the metal rod 21 by heat shrinking, when the end portion 25 is formed by the heat members 23, 24, one balloon portion 27 is formed. At this time, also, the end portion 26 of another balloon portion 27' is formed as shown in FIG. 11. After forming the end portions 25, 26, the movable heat members 23, 24 are moved away from each other as shown in FIG. 11, and the heat members 23, 24 are moved toward the direction shown by arrows 52 in FIG. 11 to form another end of the balloon portion 27'.

Figure 12:
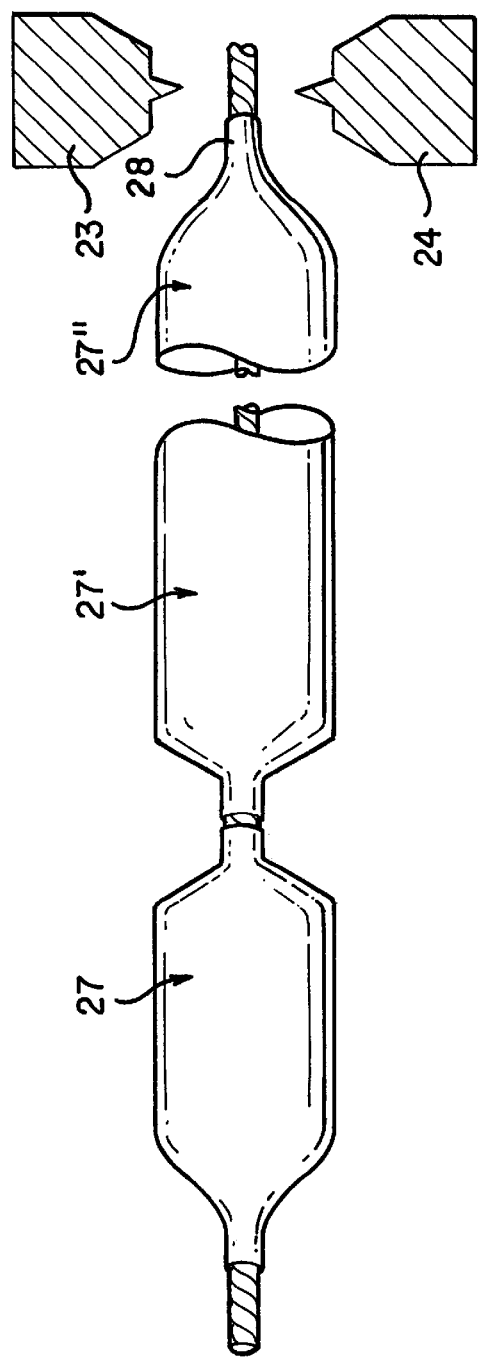
FIG. 12 is a schematic side view showing that a plurality of balloon members is formed from the heat shrinkable tube by the movable heating members.
Figure 13:
FIGS. 13–15 are schematic explanatory views for forming a conventional balloon catheter.
Figure 14:
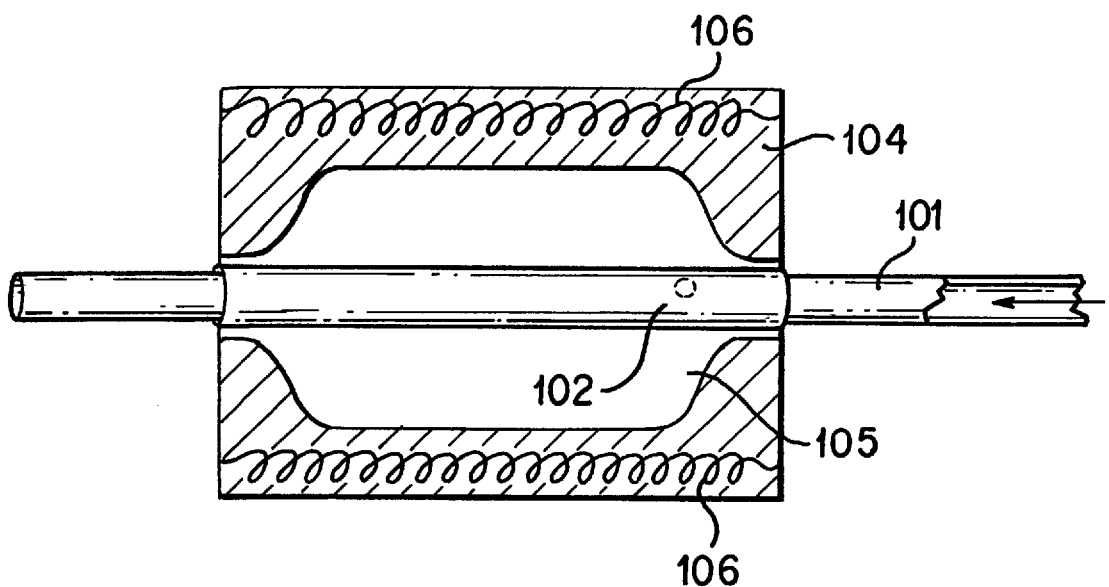
Figure 15:
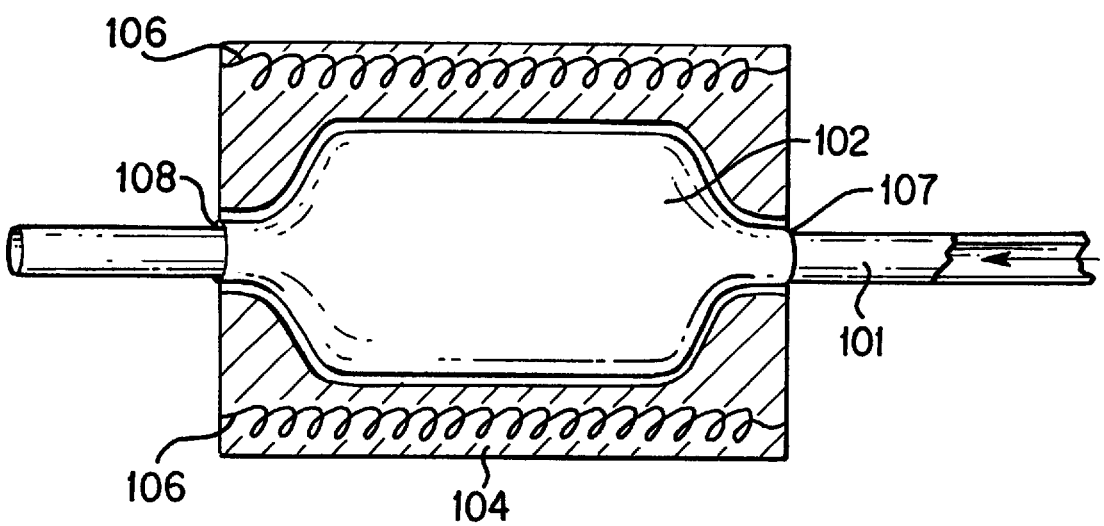

By repeating the above described steps shown in FIGS. 9–11, a plurality of balloon portions 27, 27', 27'' and so on can be formed from the single, elongated heat shrinkable tube 20 as shown in FIG. 12. An end 28 of the heat shrinkable tube 20 may be deposited on the metal rod member 21 by the heat members 23, 24, or heating the end by hot air.

In case the end 22 of the tube 20 is simply attached onto the metal rod 21 by string and the like, the first balloon portion 27 is not used, and the subsequent balloon portions shaped and cut by the heat members 23, 24 are used for forming the balloon catheter.

In the above embodiment, a pair of the heat members 23, 24 is used, but a plurality of heat members 23, 24 spaced apart from each other in the lateral direction may be used. In this case, when the heat members 23, 24 are moved at the same time in the direction to contact each other, a plurality of the balloon members is formed at once.

Each balloon portion 27 formed as described above can be attached to the catheter shaft to form the balloon catheter as in the same method described in the first embodiment.

According to the method for forming a balloon catheter of the invention, a balloon portion or member is prepared from a heat-shrink tube with an even thickness, and only both ends of the balloon member are heated to shrink. Thus, the balloon member can be formed into the shape of the balloon while the thickness of the balloon member is even throughout the entire length thereof. Therefore, the high quality balloon catheter can be formed without fail.

While the invention has been explained with reference to the specific embodiments of the invention, the explanation is illustrative and the invention is limited only by the appended claims.

What is claimed is:

1. A method of forming a balloon catheter, comprising:

preparing a heat shrinkable tube forming at least one balloon portion, said heat shrinkable tube having a first diameter, inserting a rod member into the shrinkable tube, heating parts of the shrinkable tube so that the parts of the shrinkable tube shrink to have a second diameter less than the first diameter to thereby form end portions of the at least one balloon portion while a portion away from the end portions has the first diameter, removing the rod member from the balloon portion, inserting a catheter shaft into the balloon portion to completely pass therethrough, and fixing two end portions of the balloon portion onto the catheter shaft.

2. A method of forming a balloon catheter according to claim 1, wherein said two end portions are formed by heat-shrinking the shrinkable tube.

3. A method of forming a balloon catheter according to claim 2, further comprising, insulating an outer periphery of a middle portion between the two end portions from the two end portions, and then, said heating is conducted so that said two end portions are heated to shrink while the middle portion is insulated from being heated.

4. A method of forming a balloon catheter according to claim 3, further comprising, providing a gas inside the shrinkable tube before heating to keep a shape of the shrinkable tube.

5. A method of forming a balloon catheter according to claim 3, further comprising, cooling the middle portion of the balloon portion while the end portions are heated.

6. A method of forming a balloon catheter according to claim 5, further comprising, preparing a mold for receiving the shrinkable tube for the one balloon portion, said mold having two insulating members therein to provide two end areas and a middle area between the two end areas, said shrinkable tube being located in the mold so that the middle portion is located in the middle area and the two end portions are located in the end areas, said heating being conducted in the end areas by heating the end portions.

7. A method of forming a balloon catheter according to claim 6, wherein heated gas is introduced into the end areas to shrink the end portions.

8. A method of forming a balloon catheter according to claim 1, further comprising, after the rod member is inserted into the shrinkable tube, reducing a diameter of one end of the shrinkable tube, and providing a gas into the shrinkable tube to keep a shape of the shrinkable tube in an inflated condition.

9. A method of forming a balloon catheter according to claim 8, wherein by heating the parts of the shrinkable tube, one end portion of one balloon portion and one end portion of another balloon portion are formed at the same time.

10. A method of forming a balloon catheter according to claim 9, wherein a plurality of parts away from each other of the shrinkable tube is heated at substantially the same time to form a plurality of balloon portions at substantially the same time.

11. A method of forming a balloon catheter according to claim 10, wherein said heating is conducted by heat pads formed of a plurality of heat segments, said heat segments being disposed onto the rod member through the shrinkable tube while shrinking the shrinkable tube.

12. A method of forming a balloon catheter according to claim 11, wherein said heat segments are pressed against the rod member to thereby cut the balloon portions away from each other.

* * * * *